(12) United States Patent
Burkhart

(10) Patent No.: US 6,267,766 B1
(45) Date of Patent: Jul. 31, 2001

(54) SUTURE ANCHOR REEL DEVICE KIT AND METHOD

(76) Inventor: Stephen S. Burkhart, 201 Village Cir., San Antonio, TX (US) 78232

(*) Notice: Subject to any disclaimer, the term of this patent is extended or adjusted under 35 U.S.C. 154(b) by 0 days.

(21) Appl. No.: 09/322,371

(22) Filed: May 28, 1999

(51) Int. Cl.⁷ .................................................. A61B 17/16
(52) U.S. Cl. ........................... 606/72; 606/74; 606/232
(58) Field of Search .................................. 606/72, 74, 75, 606/104, 232; 411/340

(56) References Cited

U.S. PATENT DOCUMENTS

| | | |
|---|---|---|
| 5,108,399 | 4/1992 | Eilenmoller et al. . |
| 5,116,337 | 5/1992 | Johnson . |
| 5,129,904 | 7/1992 | Illi . |
| 5,236,431 | 8/1993 | Gogolewski et al. . |
| 5,258,016 * | 11/1993 | Dipoto et al. ........................ 606/232 |
| 5,443,482 | 8/1995 | Stone et al. . |
| 5,545,180 * | 8/1996 | Le et al. ................................ 606/232 |
| 5,569,306 | 10/1996 | Thai . |
| 5,573,548 | 11/1996 | Nazre et al. . |
| 5,618,314 * | 4/1997 | Harwin et al. ........................ 606/232 |
| 5,626,613 | 5/1997 | Schmieding . |
| 5,658,313 | 8/1997 | Thai . |
| 5,665,112 | 9/1997 | Thai . |
| 5,683,419 | 11/1997 | Thai . |
| 5,707,394 | 1/1998 | Miller et al. . |
| 5,709,708 | 1/1998 | Tahi . |
| 5,720,765 | 2/1998 | Thai . |
| 5,720,766 | 2/1998 | Zang et al. . |
| 5,728,136 | 3/1998 | Thai . |
| 5,733,307 | 3/1998 | Dinsdale . |
| 5,814,070 * | 9/1998 | Bozone et al. ........................ 606/232 |
| 5,814,073 | 9/1998 | Bonutti . |
| 5,824,011 * | 10/1998 | Stone et al. ........................... 606/232 |
| 5,868,789 | 2/1999 | Huebner . |
| 5,899,920 | 5/1999 | Desatnick et al. . |
| 5,904,704 | 5/1999 | Marlowe . |
| 5,906,624 * | 5/1999 | Wenstrom, Jr. ....................... 606/139 |

* cited by examiner

Primary Examiner—Michael H. Thaler
Assistant Examiner—Lien Ngo
(74) Attorney, Agent, or Firm—Jackson Walker, LLP

(57) ABSTRACT

A suture anchor and kit for anchoring a suture member to human bone. A suture anchor includes a threaded portion and has a head at the proximal end thereof, the head being generally circular. A tip is located at a distal end of the shank. The shank is at least partially threaded and includes walls defining a reel portion. The shank also includes walls for engaging a suture, the walls for engaging the suture typically adjacent walls defining the reel portion. The head typically includes walls for engaging a drive tool. The kit includes a drive tool for rotating the suture anchor when a suture member is engaged with the walls for engaging the suture such that rotation of the anchor causes the suture material to wrap around the reel portion of the shank.

2 Claims, 5 Drawing Sheets

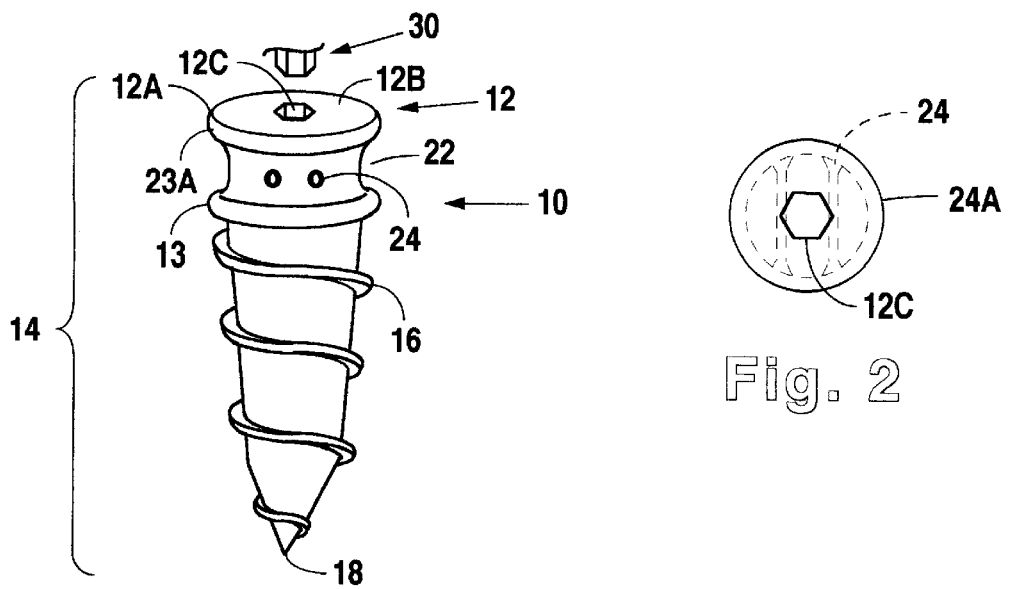
Fig. 1
Fig. 2
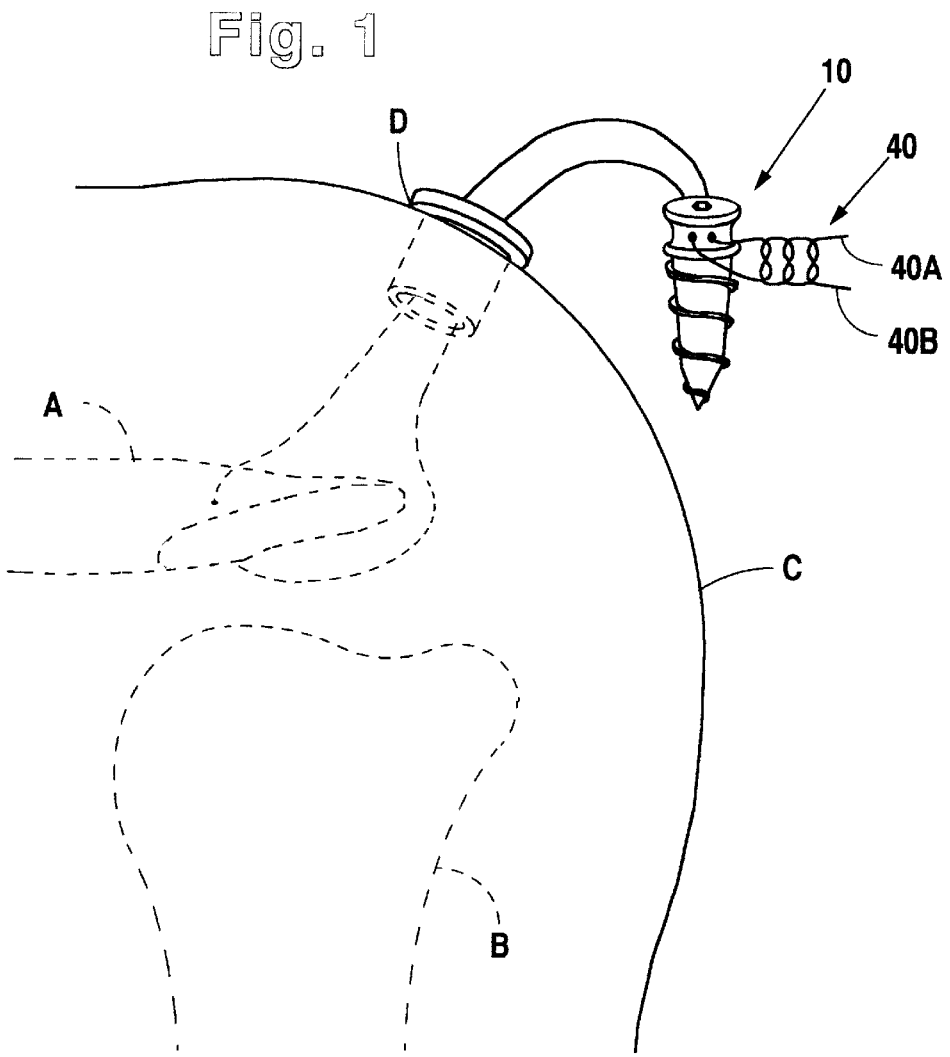
Fig. 3

SUTURE ANCHOR REEL DEVICE KIT AND METHOD

BACKGROUND OF THE INVENTION

1. Field of the Invention

Applicant's invention relates to a device, method and kit for repairing tissue, namely for selectively positioning a suture-bearing tissue adjacent a bone mass.

2. Background Information

When soft tissue, such as tendons and ligaments, are torn away from the bone, surgery may be required to repair the tear. Typically, a suture member is threaded through the torn tissue and through a tunnel drilled in the bone mass. The suture material is drawn up and tied so that the torn tissue lays adjacent the bone mass in proper position to heal.

A number of assemblies have been provided to anchor tissue to a bone mass. These devices are usually attached to the bone mass through the use of open incisions or, sometimes, arthroscopic surgical techniques. Arthroscopic surgery is advantageous compared to the use of open surgery because of the decreased pain and quicker recovery period. However, the invention may be used advantageously with open surgery as well.

The various assemblies used for attaching soft tissue to the bone include screws, staples, suture anchors, cement, and sutures alone. The suture anchor is a small device, typically insertable arthroscopically through a cannula to the repair site to anchor the suture to a bone.

That is, a suture is passed through the soft tissues and inserted into a suture anchor in the base. Such a suture anchor assembly is disclosed in U.S. Pat. No. 5,683,419. This suture anchor assembly includes two main components: an anchor sleeve, which can have a closed pointed drill end or be totally cylindrical in shape, ribbed, or threaded on its exterior for attachment to the bone; and a spike or plug with one end that allows for easy puncturing of soft tissue and a second end for attachment of the suture material. The pointed first end of the spike or plug allows it to be insertable to the sleeve, which sleeve has been inserted into the bone.

A second device is disclosed in U.S. Pat. No. 5,904,704 and includes a suture anchor assembly, including a suture anchor and a tool for deploying the suture anchor in the bone. The suture extends from and is anchored to the bone. The suture anchor has a drill portion and a thread portion, and a suture attachment portion distal to the pointed portion.

None of the prior art provides for a suture anchor that includes a reel portion adjacent suture-receiving walls in a manner that allows the threading of the anchor member into the bone while the suture material simultaneously winds around the reel portion of the suture anchor to draw up the suture and the corresponding soft tissue to which the suture is engaged so as to selectively position the soft tissue adjacent the bone.

Applicant provides a unique suture anchor, including a reel portion thereon, a unique method of using the suture anchor to selectively position, by rotation of the suture anchor and gathering the suture material on the reel portion thereof, the suture bearing tissue, and a novel kit providing a suture anchor and a tool for rotating the suture anchor. Applicant's device may be used without the necessity of tying suture knots arthroscopically or, indeed, may be used without tying suture knots at all.

Applicant's novel suture anchor, method, and kit overcome problems encountered in prior art suture anchors and provide a relatively easy method of arthroscopically reattaching torn or displaced tissue to a bone mass.

FIG. 1 is a side elevational view of the suture anchor of Applicant's present invention holes in any non-head portion.

FIG. 2 is a top elevational view of the suture anchor of FIG. 1.

FIG. 3 is a side perspective view of a shoulder C (partially cut-away) having torn tissue A therein, having a bone mass B, the shoulder open through an incision through which is inserted a cannula D, the perspective view illustrating the engagement of suture material 40 to suture anchor 10.

Figure 3A:
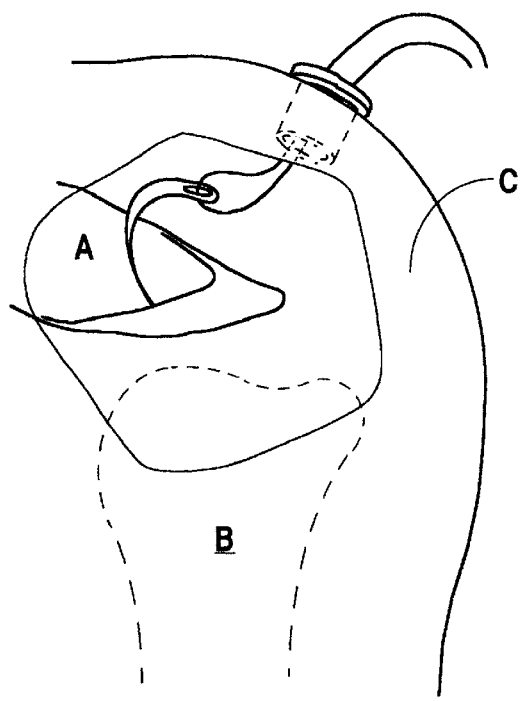
FIGS. 3A and 3B illustrate perspective views of the shoulder (partially cut-away) illustrating two steps of Applicant's present invention.
Figure 3B:
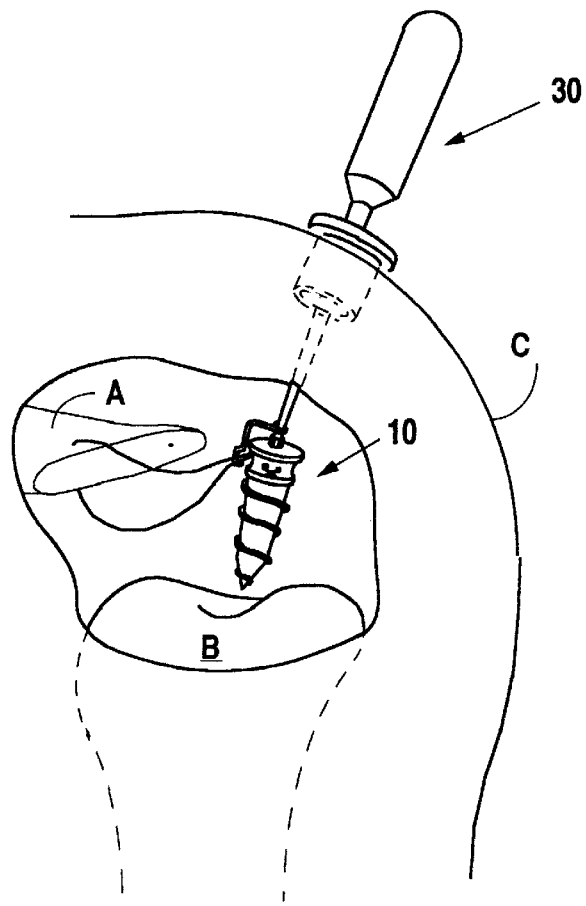
Figure 4:
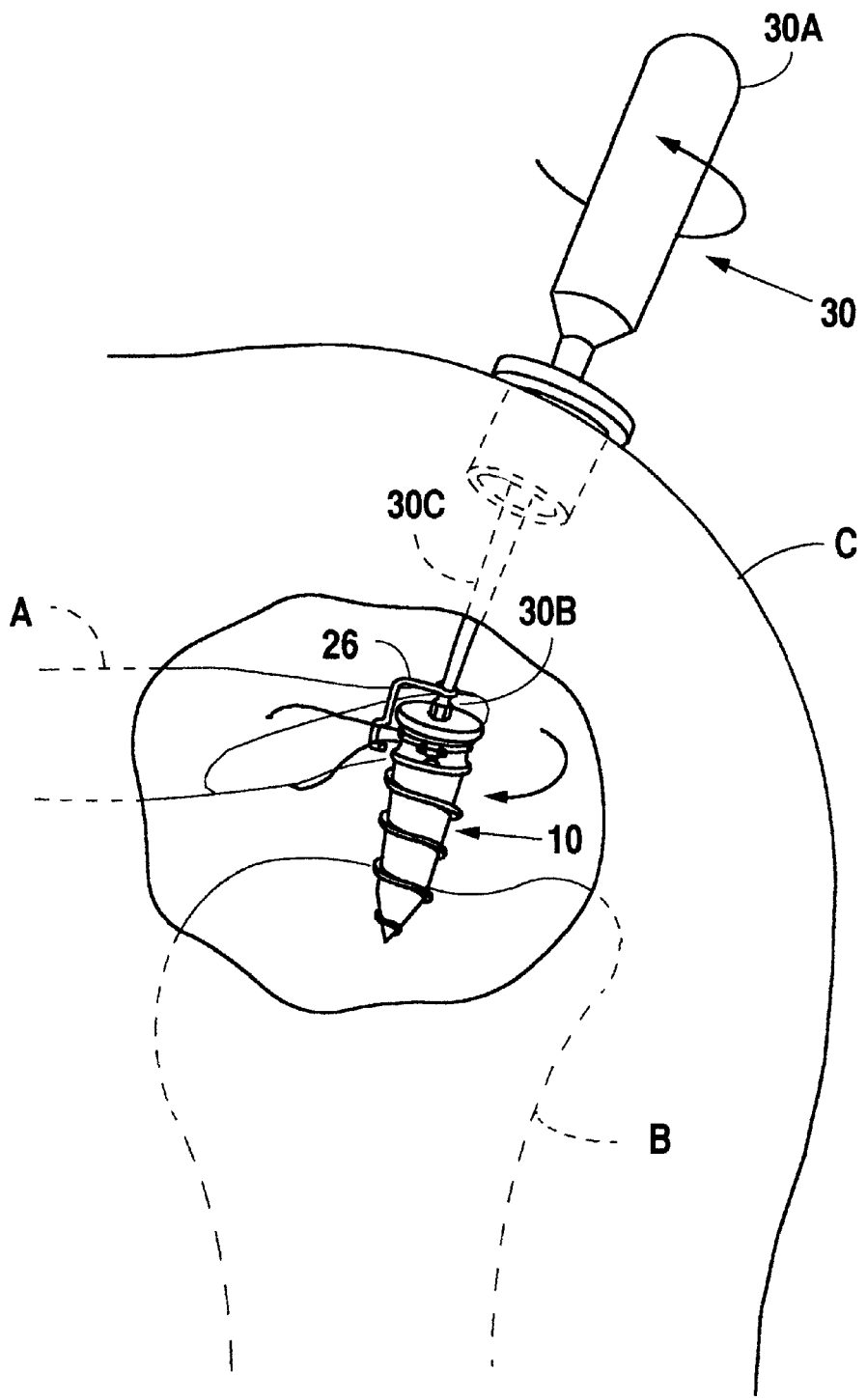

FIG. 4 is a view of the shoulder C of FIG. 3 which illustrates the use of Applicant's tool 30 for engaging the anchor 10 as the anchor is inserted into bone B, the perspective view also illustrating the use of an out-rigger 26 on the tool to help guide the suture.

Figure 5:
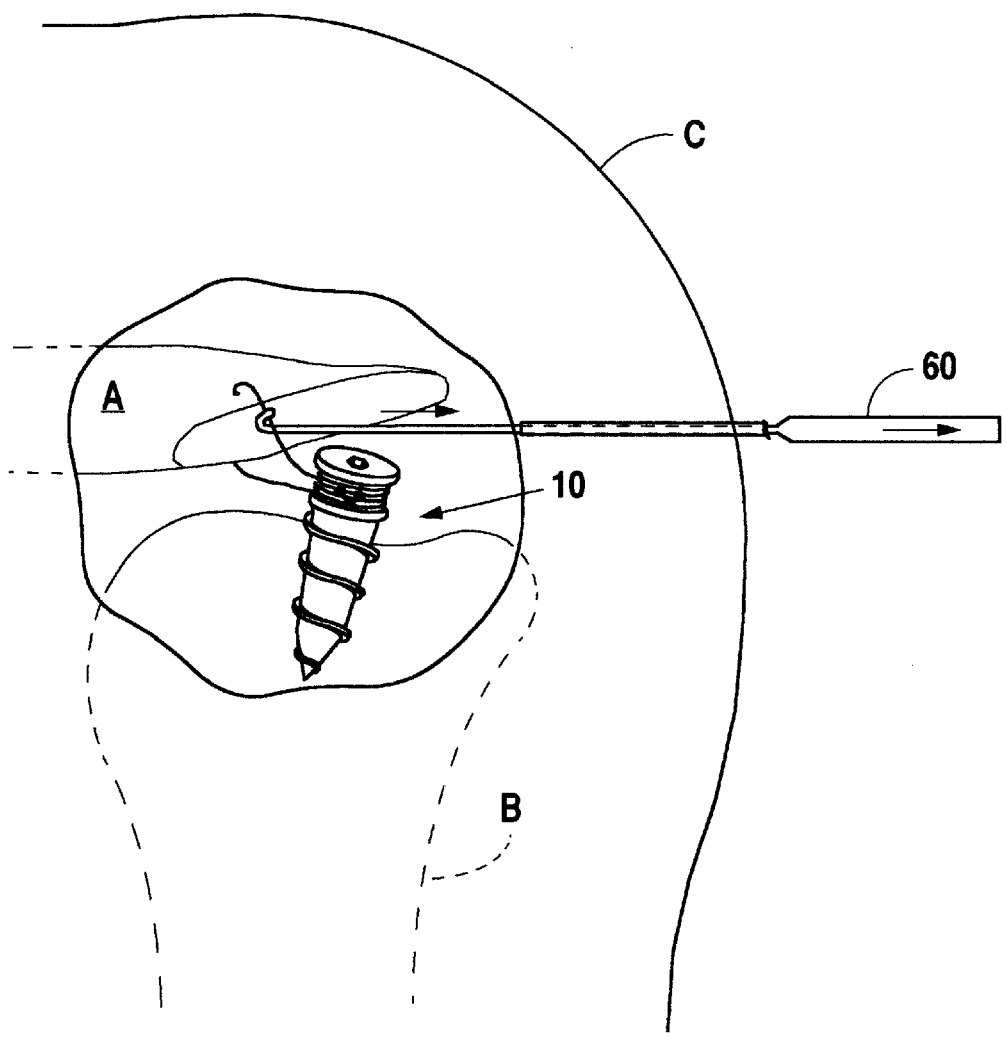

FIG. 5 is an illustration of an additional hook tool 60 for use with Applicant's present invention.

Figure 6:
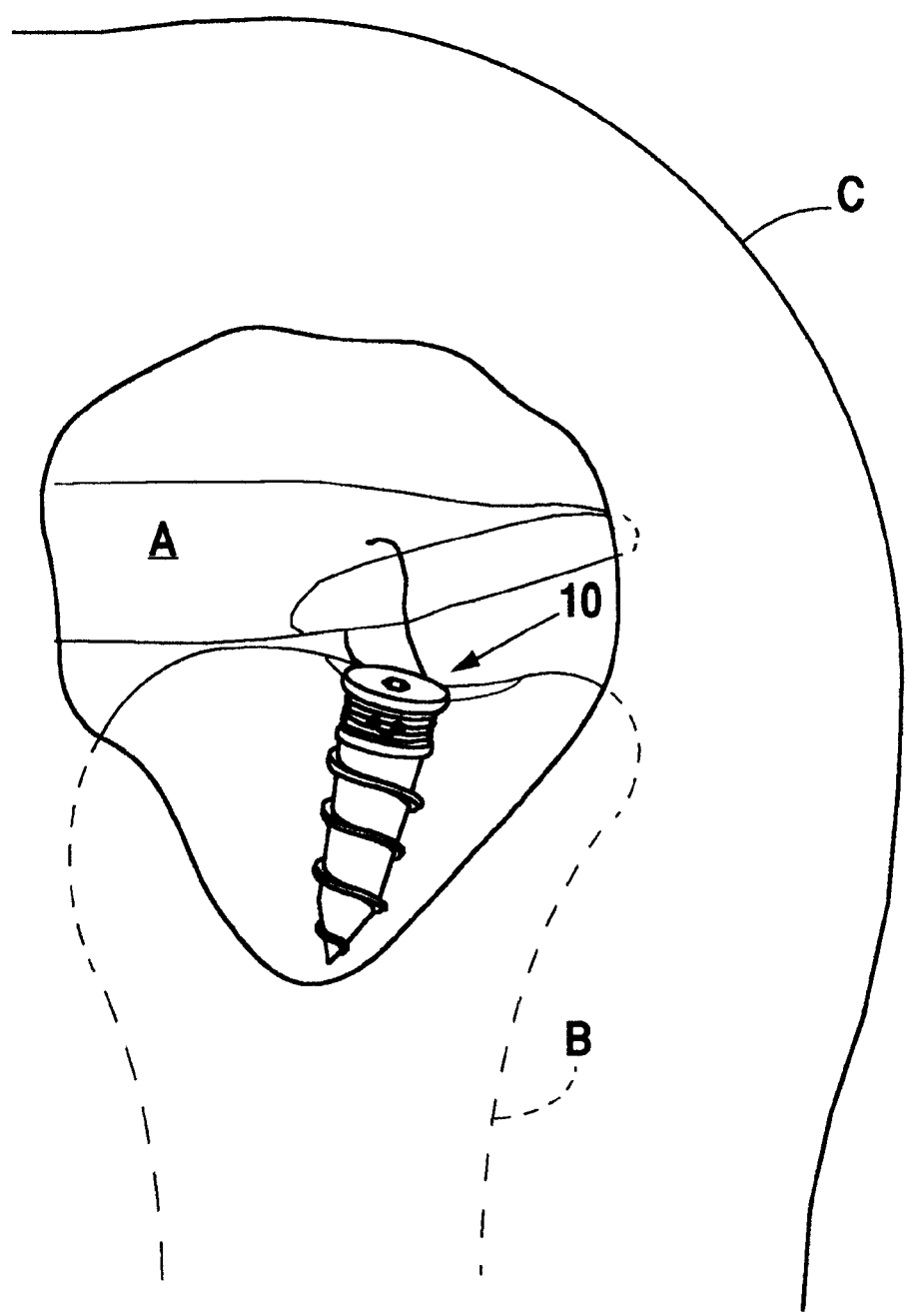

FIG. 6 illustrates the shoulder mass and tissue after the tissue has been selectively located adjacent the bone by reeling surgery material onto the suture anchor in the manner set forth in Applicant's present invention.

DETAILED DESCRIPTION OF THE PREFERRED EMBODIMENT

In viewing FIGS. 1 through 3 it is seen that Applicant's present invention includes a unitary, longitudinal suture anchor 10, typically made of titanium, stainless steel, plastic, allograft bone, or other suitable material, including a bioabsorbable material. The suture anchor is seen to have a generally circular head 12, the head typically having an outer edge 12A, an upper surface 12B, and walls 12C for engaging any type of mating tool as set forth in more detail below.

Applicant's novel suture anchor 10 includes a shank portion 14 located distal to the head 12, the shank portion 14 having threads 16 on at least a portion thereof, the shank portion 14 terminating at a tip 18. The shank portion 14 also includes a reel portion 22, typically having adjacent walls defining a suture receiving portion. The particular configuration of the walls here include a pair of holes 24 going from one portion of the outer surface of the shank portion 14 to a second portion of the outer surface of the shank portion 14 (see FIG. 2) transverse to the longitudinal axis of the shank portion 14 and being dimensioned to receive a suture member 40 therethrough. That is, the holes are in a non-head portion of the anchor.

The reel portion 22 typically has raised upper wall 23 proximal (towards the head 12) adjacent thereto to keep the gathered suture member 40 from slipping off the top of the wall. It may also have lower wall 13 which, in conjunction with upper wall, help keep the suture winding on the anchor. It is noted that the lower wall 13 in the embodiment illustrated in FIGS. 1–3 have about the same radius as the upper wall, while the lower walls in the embodiment illustrated the remaining figures have a diameter less than the upper walls.

FIGS. 1 and 2 also illustrate how the tool 30, such as the tool illustrated in FIG. 4, is used to the engage walls 12C of the head 12 in a manner such that, when the tool 30 (see FIG. 4) is engaged with the suture anchor 10 and, further, while the suture member 40 is engaged with the walls of the shank portion 14, the suture member 40 will gather on the reel portion 22 of the suture anchor 10. Further, since the suture member 40 was previously engaged with, as by threading a tissue A (see FIG. 3A illustrating open surgery rather than arthroscopic, a suture passer would be used in arthroscopic surgery) before being engaged with the suture member 40, rotation and gathering of the suture member 40 on the reel portion 22 of the suture anchor 10 will cause the tissue to move closer to the suture anchor 10 while the suture anchor 10 is being driven into bone, so as to simultaneously affix the suture anchor 10 to the bone and gather the suture member 40 onto the suture anchor 10 to position the tissue adjacent the bone at a predetermined location.

FIG. 6 illustrates the use of Applicant's novel method, device, and kit when the task of reeling up suture material is completed so as position tissue A against or adjacent bone mass B at a predetermined position flush with bone or countersunk to produce an interference fit with the suture material between the anchor and the bone. Alternatively, a portion of the reel portion may be left above the surface of the bone.

It is anticipated that Applicant's novel method, device and kit is best utilized with arthroscopic techniques through the use of cannula D, here illustrated for use on a shoulder, but capable of being used anywhere in the body where tissue is needed to be attached to a bone mass. Indeed, Applicant's method and system can be used in open surgery as well as arthroscopically. When used in arthroscopic surgery, the suture anchor 10 is usually dimensioned suitable to fit within the cannula D, as is the tool 30.

As shown in FIG. 5, a hook device 60 may be inserted through the cannula D and used when either additional suture material 40 needs to be taken up and wound around the reel manually, as when the suture anchor 10 is already seated into the bone, and the tissue needs to be brought yet closer to the anchor. Likewise, suture material may be unwound one course at a time if the surgeon feels it is necessary to allow the tissue to move further from the inserted suture anchor 10.

The following describes the novel method (open or arthroscopic) of use of Applicant's present invention. The repair site is first located after a small incision and insertion of the cannula D through the skin. The suture member 40 is threaded onto a needle (open surgery) or suture passer (arthroscopic surgery), which is transported to the repair site. The suture-bearing needle or arthroscopic instrument is passed through the tissue, and then the suture member 40 and the needle are removed through the cannula D. The suture member 40 is then engaged with the suture anchor 10 by, for example, inserting through the holes 24 in the suture anchor 10 and tied off or pulled through the hole (FIG. 3). Alternatively, the suture may pass through the hole and not be tied, but simply wound around the reel portion for a friction fit to the anchor. Next, the suture anchor 10 is transported through the cannula D to the repair site and placed adjacent the bone mass positioned selectively so that rotation and insertion of the suture anchor 10 into the bone mass, while the suture member 40 is winding onto the reel portion, will locate the tissue at a predetermined location adjacent the bone mass. If the anchor is made from a bioabsorbable material, the bone is typically pre-tapped before inserting the anchor.

Having selected the appropriate location adjacent the bone mass, the tool 30 is then inserted through the cannula D and engaged with the head of the suture anchor 10. Rotation by manually rotating the handle of the tool 30, while urging the suture anchor 10 against the bone, will seat the suture anchor 10 while the suture member 40 winds onto the reel portion 22 of the suture anchor 10. Rotation continues until the tissue is properly positioned adjacent the bone mass with anchor sunk until head upper surface is flush with cortex of bone or countersunk (see FIG. 6). This provides an interference fit holding the suture between the bone and the reel portion so the suture material will not unwind. Alternate procedures, such as using the hook tool 60 through the wind or unwind courses of the suture member 40 onto the reel portion 12, used if necessary. The tool 60 and the cannula D are then removed and the wound closed in accordance with procedures known in the art.

The surgeon may estimate the amount of take up required on the suture material to properly locate the tissue. Knowing the approximate diameter of the reel portion, the surgeon may adjust the pre-drilling length of suture between the anchor and the tissue so that when the anchor is wound into the bone to the position set forth in FIG. 6, the tissue is properly positioned.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A method for locating human tissue adjacent to human bone using a suture member, the method comprising the steps of:

providing an anchor having a tapered portion with a generally circular head at a first end and a pointed tip at a second end, the head including tool engagement walls, the anchor having at least a portion thereof having threads thereon, a shank including suture receiving walls and walls defining a reel portion, the reel portion having a diameter less than the head, the walls defining the reel portion capable of gathering a suture member thereupon when the suture member is engaged with the suture receiving walls and the shank rotated with the tool engaged to the tool engaging walls of the head of the device;

passing the suture member through the tissue;

engaging the suture member with suture receiving walls of the anchor;

inserting the distal end of the anchor into the bone;

rotating the anchor at least part way into the bone such that the suture member accumulates on the reel portion of the anchor, while moving the tissue closer to the anchor, and stopping the rotating when the tissue reaches a predetermined position adjacent the bone.

2. An open or arthroscopic method for positioning a human tissue having a suture member engaged therewith adjacent a bone mass, including the steps of:

providing a threaded anchor member having suture receiving walls and a reel portion;

engaging at least a portion of the suture member with the suture receiving walls of the anchor;

engaging the tip of the suture anchor to the bone mass; and rotating the anchor member at least part way into the bone such that the suture member winds onto the reel portion and draws the tissue material closer to the anchor member until the tissue material reaches the desired location.

* * * * *